United States Patent [19]

Yamayoshi et al.

[11] Patent Number: 5,290,917
[45] Date of Patent: Mar. 1, 1994

[54] MODIFIED POLYPEPTIDES OF IL-1α

[75] Inventors: Michiko Yamayoshi, Toyonaka; Hitoshi Kawashima, Osaka; Junichi Yamagishi, Nara; Hirotada Kotani, Sakai; Ryuji Furuta, Otsu; Toshikazu Fukui, Settsu, all of Japan

[73] Assignee: Dainippon Pharmaceutical Co., Ltd., Osaka, Japan

[21] Appl. No.: 681,077

[22] Filed: Apr. 5, 1991

Related U.S. Application Data

[63] Continuation-in-part of Ser. No. 305,461, Feb. 1, 1989, abandoned.

[51] Int. Cl.⁵ .............................................. C07K 13/00
[52] U.S. Cl. .................................. 530/351; 930/141; 424/85.2; 435/69.52; 435/69.5
[58] Field of Search ................... 530/351; 930/141; 435/69.5, 69.52

[56] References Cited

U.S. PATENT DOCUMENTS

| | | | |
|---|---|---|---|
| 5,017,692 | 5/1991 | Zurowaski | 435/69.52 |
| 5,047,505 | 9/1991 | Huang | 530/351 |
| 5,093,242 | 3/1992 | Bachmair et al. | 435/69.52 |

FOREIGN PATENT DOCUMENTS

| | | |
|---|---|---|
| 0188920 | 7/1986 | European Pat. Off. |
| 0200986 | 11/1986 | European Pat. Off. |
| 0237073 | 9/1987 | European Pat. Off. |
| 0259160 | 3/1988 | European Pat. Off. |

OTHER PUBLICATIONS

March et al, *Nature*, 315, 1985, pp. 641-647.
Mosley et al., *PNAS* 84, 1987, pp. 4572-4576.
Gronenborn et al, *FEB* 231, 1988, pp. 135-138.
Wingfield et al, *Protein Engineering* 1(5) 1987, pp. 413-417.
DeChiara et al, *PNAS* 83, 1986, pp. 8303-8307.
Wells et al, *Gene* 34, 1985, pp. 315-323.
Daumy et al, Biochem. Biophys Acta, vol. 998, 1989, pp. 32-42.
Zurawski, et al. (1986) *Gene* 49:61-68, Expression in *Excherichia coli* of Synthetic Human Interleukin-1α Genes Encoding the Processed Active Protein, Mutant Proteins, and β-Galactosidase Fusion Proteins.
Hopp, et al. (1986) *Immunol. Res.* 5:271-280, The Molecular Forms of Interleukin-1.
Huang, et al. (1987) *FEBS Lett.* 223: 294-298, Muteins of Human Interleukin-1 that Show Enhanced Bioactivities.
Cameron, et al. (1986) *J. Exp. Med.* 164:237-250, Purification to Homogeneity and Amino Acid Sequence Analysis of Two Anionic Species of Human Interleukin 1.

Primary Examiner—Garnette D. Draper
Attorney, Agent, or Firm—Scully, Scott, Murphy & Presser

[57] ABSTRACT

Novel polypeptides having a modified amino acid sequence of human interleukin 1α polypeptides in which a certain amino acid residue(s) in said amino acid sequence is(are) exchanged for other amino acid residue(s). Said polypeptides having no capacity of induction of production of prostaglandin $E_2$ while maintaining other biological activities of human interleukin 1 such as activation of lymphocyte and being expected to be useful as a medicament.

3 Claims, 3 Drawing Sheets

MODIFIED POLYPEPTIDES OF IL-1α

This application is a continuation-in-part application of U.S. Ser. No. 305,461 filed on Feb. 1, 1989, now abandoned.

This invention relates to novel polypeptides having a modified amino acid sequence of human interleukin 1 in which the N-terminal and C-terminal regions may optionally be deleted, that is, a certain amino acid residue(s) in said amino acid sequence being exchanged for other amino acid residue(s), and a DNA encoding the modified amino acid sequence, and a process for producing said polypeptides and said DNA.

Prior Art

Interleukin 1 is a physiologically active substance produced in various cells such as monocytic/macrophage cells. It is known that human interleukin 1 includes generally two types of polypeptides of α-type and β-type (cf. Furutani, Y. et al., Nucleic Acids Res., Vol. 14, 3167, 1986; Clark, B. D. et al., Nucleic acids Res., Vol. 14, 7897, 1986). It is also known that the interleukin 1 has activities such as promotion of proliferation of T and B lymphocytes, activation of lymphocyte, activation of macrophage, function of endogenous pyrogens, induction of production of prostaglandin $E_2$, and promotion of proliferation of fibroblast, and the like (cf. Oppenheim, J. J. et al., Immunology Today, Vol. 7, 45, 1986; Dinarello, C. A., Reviews of Infectious Diseases, Vol. 6, 51, 1984). Thus, interleukin 1 takes an important role on the control of immunological mechanism in living body and is expected to be clinically useful as a medicament.

There are known some derivatives of α-type human interleukin 1 polypeptide, such as human interleukin 1α polypeptide in which one to fourteen amino acid residues at the N-terminus and/or one to four amino acid residues at the C-terminus are deleted (cf. European Patent Publication 0188920) and human interleukin 1α polypeptide in which 36th amino acid (Asn) at the N-terminus is deamidated or exchanged for Asp (cf. Cameron, P. M. et al., J. Exp. Med., Vol. 164, 237, 1986; Wingfield, P. et al., Eur. J. Biochem., Vol. 165, 537, 1987) There is also known a modified polypeptide of α-type human interleukin 1 originated from other gene in which second amino acid residue (Ser) at the N-terminus is exchanged for Ala (cf. March, C. J. et al., Nature, Vol. 315, 641, 1985). As to β-type human interleukin 1 polypeptide, there are known derivatives of the polypeptide in which one to three amino acid residues at the N-terminus and/or one to three amino acid residues at the C-termunus are deleted (cf. Mosley, B. et al, Proc. Natl. Acad. Sci. USA, Vol. 84, 4572, 1987).

BRIEF DESCRIPTION OF THE INVENTION

The present inventors have investigated the relationship between the chemical structure of human interleukin 1 and the biological activities thereof and the activities of modified polypeptide in which a cetain portion of the amino acid sequnece is exchanged for other amino acid residue(s) and have unexpectedly found that some modified polypeptides show almost no induction of production of prostaglandin $E_2$ while they show activation of lymphocyte.

An object of the invention is to provide a modified polypeptide of human interleukin 1 polypeptide in which a part of the amino acid sequence is exchanged for other amino acid residue and further a certain amino acid residue(s) at the N-terminus and/or the C-terminus are optionally deleted. Another object of the invention is to provide DNA encoding the modified polypeptide. A further object of the invention is to provide a process for producing the polypeptide and the DNA. These and other objects and advantages of this invention will be apparent to those skilled in the art from the following description.

DETAILED DESCRIPTION OF THE INVENTION

Figure 1:
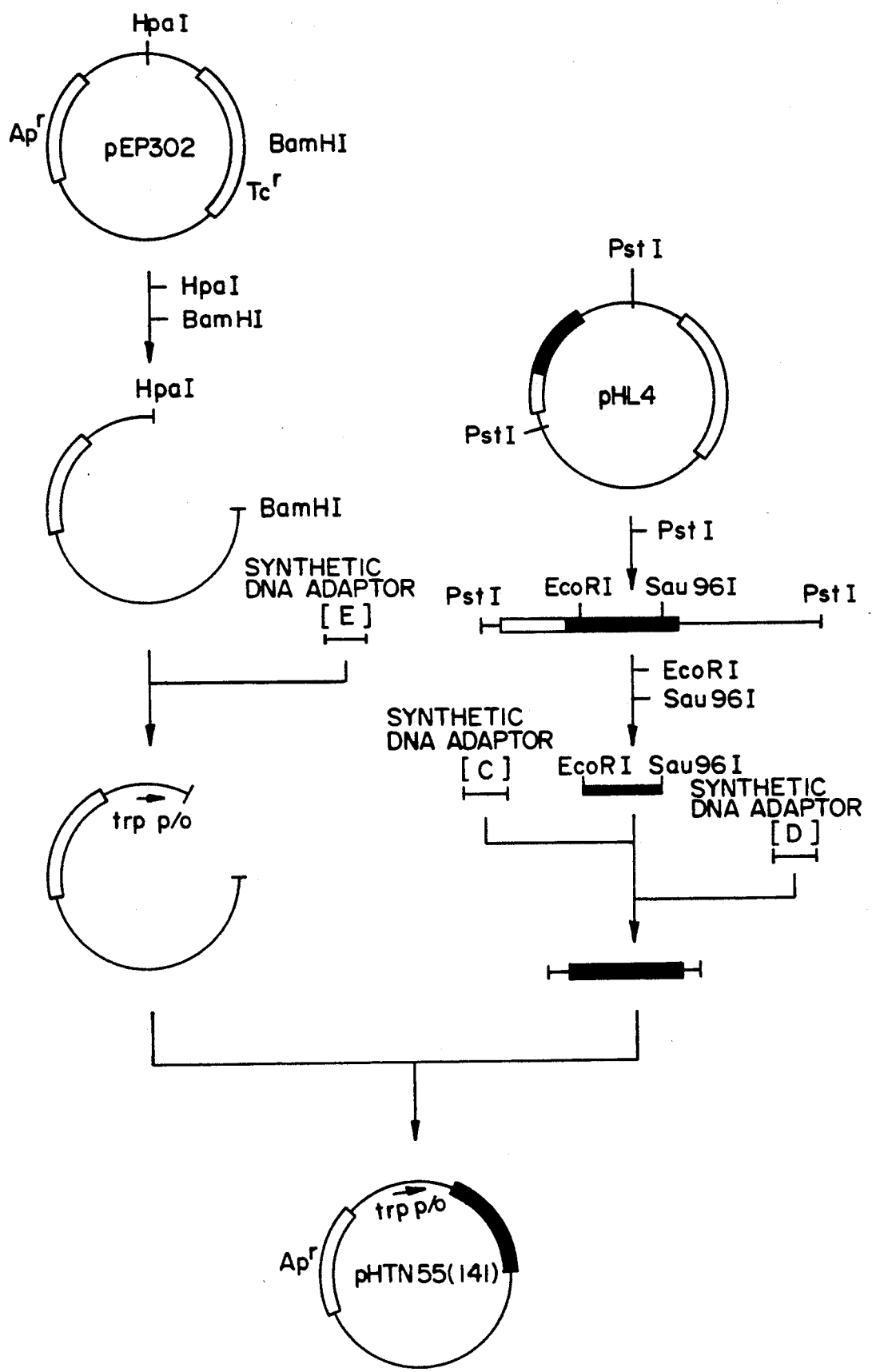
FIG. 1 shows steps of the construction of expression plasmid pHTN55(141) of this invention, wherein the synthetic DNA adaptors [C], [D] and [E] are the chemically synthesized oligonucleotide adaptors as described in Example 3.

The modified polypeptide of this invention includes human interleukin 1α polypeptide in which partial amino acid residues are exchanged for other amino acid residue(s), i.e. a polypeptide having amino acid sequence of the formula [I] in Table 1 in which one to fourteen amino acid residues or peptide at the N-terminus and/or one to four amino acid residues or peptide at the C-terminus are optionally deleted.

TABLE 1

Formula [I]

| | | | | | | | | | |
|---|---|---|---|---|---|---|---|---|---|
| Ser | W | Pro | Phe | Ser | Phe | Leu | Ser | Asn | Val |
| Lys | Tyr | Asn | Phe | Met | Arg | Ile | Ile | Lys | Tyr |
| Glu | Phe | Ile | Leu | Asn | Asp | Ala | Leu | Asn | Gln |
| Ser | Ile | Ile | Arg | Ala | X | Asp | Gln | Tyr | Leu |
| Thr | Ala | Ala | Ala | Leu | His | Asn | Leu | Asp | Glu |
| Ala | Val | Lys | Phe | Asp | Met | Gly | Ala | Tyr | Lys |
| Ser | Ser | Lys | Asp | Asp | Ala | Lys | Ile | Thr | Val |
| Ile | Leu | Arg | Ile | Ser | Lys | Thr | Gln | Leu | Tyr |
| Val | Thr | Ala | Gln | Asp | Glu | Asp | Gln | Pro | Val |
| Leu | Leu | Lys | Glu | Met | Pro | Glu | Ile | Pro | Lys |
| Thr | Ile | Thr | Gly | Ser | Glu | Thr | Asn | Leu | Leu |
| Phe | Phe | Trp | Glu | Thr | His | Gly | Thr | Lys | Asn |
| Tyr | Phe | Thr | Ser | Val | Ala | His | Pro | Asn | Leu |
| Phe | Ile | Ala | Thr | Lys | Gln | Asp | Tyr | Trp | Val |
| Cys | Leu | Ala | Gly | Gly | Pro | Pro | Ser | Ile | Thr |
| Y | Phe | Gln | Ile | Leu | Glu | Asn | Gln | Ala | | in which W means Ser or Ala, X means Asn or Asp, and Y means an amino acid residue other than Asp.

The modified polypeptide of this invention includes also human interleukin 1β polypeptide in which a certain amino acid residue(s) is(are) exchanged for other amino acid residue(s), i.e. a polypeptide of the formula [II] in Table 2 in which one to three amino acid residues or peptide at the N-terminus and/or one to three amino acid residues or peptide at the C-terminus are optionally deleted.

TABLE 2

Formula [II]

| | | | | | | | | | |
|---|---|---|---|---|---|---|---|---|---|
| Ala | Pro | Val | Arg | Ser | Leu | Asn | Cys | Thr | Leu |

TABLE 2-continued

| Arg | Asp | Ser | Gln | Gln | Lys | Ser | Leu | Val | Met |
|---|---|---|---|---|---|---|---|---|---|
| Ser | Gly | Pro | Tyr | Glu | Leu | Lys | Ala | Leu | His |
| Leu | Gln | Gly | Gln | Asp | Met | Glu | Gln | Gln | Val |
| Val | Phe | Ser | Met | Ser | Phe | Val | Gln | Gly | Glu |
| Glu | Ser | Asn | Asp | Lys | Ile | Pro | Val | Ala | Leu |
| Gly | Leu | Lys | Glu | Lys | Asn | Leu | Tyr | Leu | Ser |
| Cys | Val | Leu | Lys | Asp | Asp | Lys | Pro | Thr | Leu |
| Gln | Leu | Glu | Ser | Val | Asp | Pro | Lys | Asn | Tyr |
| Pro | Lys | Lys | Lys | Met | Glu | Lys | Arg | Phe | Val |
| Phe | Asn | Lys | Ile | Glu | Ile | Asn | Asn | Lys | Leu |
| Glu | Phe | Glu | Ser | Ala | Gln | Phe | Pro | Asn | Trp |
| Tyr | Ile | Ser | Thr | Ser | Gln | Ala | Glu | Asn | Met |
| Pro | Val | Phe | Leu | Gly | Gly | Thr | Lys | Gly | Gly |
| Gln | Asp | Ile | Thr | Z | Phe | Thr | Met | Gln | Phe |
| Val | Ser | Ser |     |     |     |     |     |     |     | wherein Z is an amino acid residue other than Asp.

The preferred polypeptides of this invention are th polypeptide of the formula [I] in Table 1 wherein W is Ser, X is Asn, and Y is Tyr, Phe, Lys or Arg, and the polypeptides having the amino acid sequence of the formula [III] in Table 3.

TABLE 3

Formula [III]

| Met | Arg | Ile | Ile | Lys | Tyr | Glu | Phe | Ile | Leu |
|---|---|---|---|---|---|---|---|---|---|
| Asn | Asp | Ala | Leu | Asn | Gln | Ser | Ile | Ile | Arg |
| Ala | X | Asp | Gln | Tyr | Leu | Thr | Ala | Ala | Ala |
| Leu | His | Asn | Leu | Asp | Glu | Ala | Val | Lys | Phe |
| Asp | Met | Gly | Ala | Tyr | Lys | Ser | Ser | Lys | Asp |
| Asp | Ala | Lys | Ile | Thr | Val | Ile | Leu | Arg | Ile |
| Ser | Lys | Thr | Gln | Leu | Tyr | Val | Thr | Ala | Gln |
| Asp | Glu | Asp | Gln | Pro | Val | Leu | Leu | Lys | Glu |
| Met | Pro | Glu | Ile | Pro | Lys | Thr | Ile | Thr | Gly |
| Ser | Glu | Thr | Asn | Leu | Leu | Phe | Phe | Trp | Glu |
| Thr | His | Gly | Thr | Lys | Asn | Tyr | Phe | Thr | Ser |
| Val | Ala | His | Pro | Asn | Leu | Phe | Ile | Ala | Thr |
| Lys | Gln | Asp | Tyr | Trp | Val | Cys | Leu | Ala | Gly |
| Gly | Pro | Pro | Ser | Ile | Thr | Y | Phe | Gln | Ile |
| Leu |     |     |     |     |     |     |     |     |     | wherein X is Asn or Asp and Y is Tyr.

This invention provides also derivatives of the above polypeptides, which mean derivatives formed by using the functional groups on the polypeptide chain, the N-terminal amino group, or the C-terminal carboxyl group, for example, esters of the carboxyl group with an aliphatic alcohol, acid amide derivatives with primary or secondary amines, N-acyl derivatives on the amino group, O-acyl derivative on the hydroxyl group, hydrolysate of carbamoyl group or modified product with polyethylene glycol. The derivatives include also salts of the carboxyl or amino group in the polypeptides with bases or acids (e.g. potassium hydroxide, arginine, caffein, procaine, hydrochloric acid, gluconic acid, etc.).

The polypeptide of this invention may optionally form a higher molecular weight compound by an intramolecular S—S bonding thereof. Such higher molecular weight compounds are also included in the polypeptide of this invention. Moreover, the polypeptide of this invention may include such a polypeptide as being added with Met at the N-terminus which is produced depending on the kinds of cells or conditions for production thereof.

This invention provides also DNAs encoding the polypeptides of this invention. The DNAs include, for example, a DNA encoding the polypeptide having an amino acid sequence of the formula [IV] in Table 4 (hereinafter, said polypeptide being referred to as "TN-55 polypeptide"), i.e. a DNA having a nucleotide sequence of the formula [A] in Table 5, and degeneration thereof.

TABLE 4

Formula [IV]

| Ser | Ser | Pro | Phe | Ser | Phe | Leu | Ser | Asn | Val |
|---|---|---|---|---|---|---|---|---|---|
| Lys | Tyr | Asn | Phe | Met | Arg | Ile | Ile | Lys | Tyr |
| Glu | Phe | Ile | Leu | Asn | Asp | Ala | Leu | Asn | Gln |
| Ser | Ile | Ile | Arg | Ala | Asn | Asp | Gln | Tyr | Leu |
| Thr | Ala | Ala | Ala | Leu | His | Asn | Leu | Asp | Glu |
| Ala | Val | Lys | Phe | Asp | Met | Gly | Ala | Tyr | Lys |
| Ser | Ser | Lys | Asp | Asp | Ala | Lys | Ile | Thr | Val |
| Ile | Leu | Arg | Ile | Ser | Lys | Thr | Gln | Leu | Tyr |
| Val | Thr | Ala | Gln | Asp | Glu | Asp | Gln | Pro | Val |
| Leu | Leu | Lys | Glu | Met | Pro | Glu | Ile | Pro | Lys |
| Thr | Ile | Thr | Gly | Ser | Glu | Thr | Asn | Leu | Leu |
| Phe | Phe | Trp | Glu | Thr | His | Gly | Thr | Lys | Asn |
| Tyr | Phe | Thr | Ser | Val | Ala | His | Pro | Asn | Leu |
| Phe | Ile | Ala | Thr | Lys | Gln | Asp | Tyr | Trp | Val |
| Cys | Leu | Ala | Gly | Gly | Pro | Pro | Ser | Ile | Thr |
| Tyr | Phe | Gln | Ile | Leu | Glu | Asn | Gln | Ala |     |

TABLE 5

Formula [A]

```
5'-TCA TCA CCT TTT AGC TTC CTG AGC AAT GTG
    AAA TAC AAC TTT ATG AGG ATC ATC AAA TAC
    GAA TTC ATC CTG AAT GAC GCC CTC AAT CAA
    AGT ATA ATT CGA GCC AAT GAT CAG TAC CTC
    ACG GCT GCT GCA TTA CAT AAT CTG GAT GAA
    GCA GTG AAA TTT GAC ATG GGT GCT TAT AAG
    TCA TCA AAG GAT GAT GCT AAA ATT ACC GTG
    ATT CTA AGA ATC TCA AAA ACT CAA TTG TAT
    GTG ACT GCC CAA GAT GAA GAC CAA CCA GTG
    CTG CTG AAG GAG ATG CCT GAG ATA CCC AAA
    ACC ATC ACA GGT AGT GAG ACC AAC CTC CTC
    TTC TTC TGG GAA ACT CAC GGC ACT AAG AAC
    TAT TTC ACA TCA GTT GCC CAT CCA AAC TTG
    TTT ATT GCC ACA AAG CAA GAC TAC TGG GTG
    TGC TTG GCA GGG GGG CCA CCC TCT ATC ACT
    TAC TTT CAG ATA CTG GAA AAC CAG GCG-3'
```

The DNA encoding the polypeptide of this invention can be obtained by preparing a DNA encoding the known human interleukin 1 polypeptide in which the amino acid residue(s) or peptide at the N-terminus and/or the C-terminus may optionally be deleted by a known method, for example by a method disclosed in the above-mentioned European Patent Publication 0188920 and then varying it partially by a method of Wang et al. (cf. Wang, A. M. et al., Science, Vol. 224, 1431, 1984) or by a method of Kunkel et al. (cf. Kunkel, T. A. et al., Methods in Enzymol., Vol. 154, 367, (1987) or alternatively by isolating an appropriate DNA segment with an appropriate restriction enzyme and combining it with a synthetic oligodeoxynucleotide adaptor in which the desired part(s) of the nucleotide sequence is(are) artificially modified.

These DNAs are inserted into an appropriate expression vector for transformation in the desired sequence by a known method, transforming a host with the expression vector, and cultivating the resulting transformant, by which the desired polypeptide can be produced. For instance, an expression vector for the production of the polypeptide of this invention can be constructed by preparing a DNA fragment containing the nucleotide sequence encoding the polypeptide of this invention in which the translation initiation codon ATG is added to the 5'-terminus and a termination codon is added to the 3'-terminus, ligating the resultant DNA fragment with an appropriate promoter and the Shine-Dalgarno (SD) sequence, and inserting the resultant into a vector. The promoter includes, for example, lac, trp, tac, phoS, phoA, PL, SV40 early stage promoter, and the like. The vector includes, for example, plasmids (e.g. pBR322 plasmid, etc.), phages (e.g. ; phage derivative, etc.), viruses (e.g. SV40 etc.), runaway plasmid, and the like.

The expression vector for the production of the polypeptide of this invention is then introduced into an appropriate host (e.g. *Escherichia coli*) by a method of Cohen et al. (cf. Cohen, S. N., et al., Proc. Natl. Acad. Sci., USA, Vol. 69, 2110, 1972) to give a transformant. The transformant is cultivated under suitable cultivation conditions to give the desired polypeptide or a polypeptide with Met at the N-terminus. The host cells in the culture broth thus obtained is destroyed, for example, by lysozyme digestion and freezing and thawing or sonication, or by using a French press, and then centrifuged or filtered to collect the extract of the polypeptide of this invention.

The polypeptide thus obtained can be purified by conventional purifying methods for proteins, for example, by ultrafiltration, dialysis, electrophoresis, salting out, gel filtration, ion exchange chromatography, affinity chromatography with an antibody column, and the like.

The derivatives of the polypeptide of this invention can also be prepared by chemically modifying the polypeptide obtained above.

As to TN-55 polypeptide having the amino acid sequence shown in Table 4, which is the representative example of the polypeptide of this invention, there are shown the various properties thereof below.

EXPERIMENT 1

Physicochemical properties of TN-55 polypeptide:

The molecular weight and isolectric point were measured as follows.

The molecular weight was 18±1 kD when measured by sodium dodecyl sulfate (SDS)-polyacrylamide gel electrophoresis, and the isoelectric point was 5.7±0.2 when measured by an isoelectric focusing.

The partial amino acid sequence of TN-55 polypeptide was determined as follows.

The polypeptide was previously treated with 4-vinylpyridine and then subjected to an enzymolysis with lysylendopeptidase (manufactured by Wako Junyaku, Japan) in the presence of urea at 35° C. overnight and the resulting peptide fragment was isolated by high performance liquid chromatography with SynChro Pack RP-P 300 column (manufactured by SynChrom Co., USA). As to the peptide fragment thus obtained and the polypeptide without being treated with a proteinase, the amino acid sequence was determined with an automatic amino acid sequencer (470A Protein Sequencer, manufactured by Applied Biosystems Co., USA).

The amino acid sequence of the proteinase-untreated TN-55 polypeptide from the N-terminus to 40th amino acid residue was determined as follows, which was completely identical with the amino acid sequence shown in Table 4.

| Ser | Ser | Pro | Phe | Ser | Phe | Leu | Ser | Asn | Val |
|-----|-----|-----|-----|-----|-----|-----|-----|-----|-----|
| Lys | Tyr | Asn | Phe | Met | Arg | Ile | Ile | Lys | Tyr |
| Glu | Phe | Ile | Leu | Asn | Asp | Ala | Leu | Asn | Gln |
| Ser | Ile | Ile | Arg | Ala | Asn | Asp | Gln | Tyr | Leu |

On the other hand, the two kinds of peptide fragments obtained by the above treatment with a proteinase (designated LP-10 fragment and LP-12 fragment, respectively) showed the following amino acid sequences, respectively. Amino acid sequence of LP-10 fragment:

| Thr | Ile | Thr | Gly | Ser | Glu | Thr | Asn | Leu | Leu |
|-----|-----|-----|-----|-----|-----|-----|-----|-----|-----|
| Phe | Phe | Trp | Glu | Thr | His | Gly | Thr | Lys | |

Amino acid sequence of LP-12 fragment:

| Gln | Asp | Tyr | Trp | Val | Cys | Leu | Ala | Gly | Gly |
|-----|-----|-----|-----|-----|-----|-----|-----|-----|-----|
| Pro | Pro | Ser | Ile | Thr | Tyr | Phe | Gln | Ile | Leu |
| Glu | Asn | Gln | Ala | | | | | | |

These amino acid sequences of LP-10 fragment and LP-12 fragment were identical with the amino acid sequences of the 101st to 119th region and the 136th to 159th region at the N terminus in Table 4.

EXPERIMENT 2

Biological Activities of TN-55 Polypeptide (1) Activation of Lymphocyte

The activation of lymphocyte was measured by the following method. That is, an aqueous solution of TN-55 polypeptide was diluted with a tissue culture medium (RPMI-1640 medium, manufactured by Flow Labs., USA) which contained 5 % bovine fetal serum. The diluted solution (each 50 μl) was poured into wells of a flat bottomed plate with 96 wells, and to each well was added phytohemaglutinine-P (manufactured by Difco Labs., USA, concentration 20 μg/ml) (each 50 μl) and thereto was further added a suspension of thymic cells of C3H/He mouse ($200 \times 10^4$ cell/ml) (each 100 μl), which was cultivated in 5% $CO_2$-air at 37° C. for 3 days. About 18 hours before completion of the cultivation, $^3H$-thymidine (1 μCi) was added, and the uptake amount of $^3H$-thymidine in cells was measured. In the negative control, RPMI-1640 medium containing 5% bovine fetal serum was added instead of test sample, and the uptake amount of $^3H$-thymidine in the cultivated thymic cells of mouse was measured likewise. The results are shown in Table 6. As is clear from the results, the TN-55 polypeptide shows potent activity for activation of lymphocyte.

TABLE 6

| Final dilution fold of TN-55 polypeptide | Uptake amount of $^3H$-thymidine |
|---|---|
| 5,000 | 94,171 cpm |
| 20,000 | 95,283 |
| 50,000 | 83,579 |
| 200,000 | 69,471 |
| 500,000 | 65,143 |
| 2,000,000 | 39,050 |
| 5,000,000 | 16,630 |
| 20,000,000 | 9,952 |
| 50,000,000 | 6,311 |
| Negative control | 6,740 |

(2) Capacity of Promotion of Production of Prostaglandin $E_2$

As to the aqueous solution of TN-55 polypeptide used in the above measurement of activation of lymphocyte, the capacity of induction of production of prostaglandin $E_2$ of TN-55 polypeptide was measured by using as a target cell human osteosarcoma MG-63 cells (American Type Cell Collection CRL 1427) as follows. That is, an aqueous solution of TN-55 polypeptide was diluted with a tissue culture medium MEM Earle (manufactured by Flow Labs.) which contained 10% bovine fetal serum, non-essential amino acids and sodium pyruvate. Each diluted solution (each 100 μl) was poured into wells of a flat bottomed plate with 24 wells, and to each well was added a cell suspension containing MG-63 cells (about 2×10⁴ cells) (each 400 μl), which was cultivated in 5% $CO_2$-air at 37° C. for 48 hours. After completion of the cultivation, the conditioned medium was separated, and the content of prostaglandin $E_2$ in the conditioned medium was measured with RIA kit (manufactured by E. I. duPont de Nemours & Co., USA). In the negative control, the above culture medium was added instead of the test solution, and the content of prostaglandin $E_2$ in the conditioned medium of MG-63 cells was measured likewise.

The results are shown in Table 7. As is clear from the results, this polypeptide shows almost no capacity of induction of production of prostaglandin $E_2$.

TABLE 7

| Final dilution fold of TN-55 polypeptide | Content of produced prostaglandin $E_2$ (ng/ml) |
| --- | --- |
| 500 | 0.36 |
| 5,000 | 0.30 |
| 50,000 | 0.18 |
| 500,000 | 0.18 |
| 5,000,000 | 0.21 |
| 50,000,000 | 0.18 |
| Negative control | 0.18 |

As to other preferred polypeptides of this invention, that is, the polypeptides of the formula (I) in Table 1 wherein W is Ser, X is Asn, and Y is Phe, Lys or Arg which are designated as "TN-55(F) polypeptide", "TN-55(K) polypeptide", and "TN-55(R) polypeptide", respectively, the biological activities thereof are shown below.

EXPERIMENT 3

Biological Activities of TN-55(F) polypeptide, TN-55(K) Polypeptide and TN-55(R) Polypeptide (1) Activation of Lymphocyte The activity for activation of lymphocyte was measured by the method described in Experiment 2. The results are shown in Table 8. As is clear from the results, the TN-55(F) polypeptide, TN-55(K) polypeptide and TN-55(R) polypeptide show activity for activation of lymphocyte.

TABLE 8

| Polypeptide | Final dilution fold | Uptake amount of ³H-thymidine |
| --- | --- | --- |
| TN-55(F) polypeptide | 1,000 | 28,549 cpm |
|  | 10,000 | 19,858 |
|  | 100,000 | 7,025 |
|  | 1,000,000 | 1,719 |
|  | 10,000,000 | 1,156 |
| TN-55(K) polypeptide | 1,000 | 9,698 cpm |
|  | 10,000 | 9,886 |
|  | 100,000 | 3,267 |
|  | 1,000,000 | 1,194 |
|  | 10,000,000 | 1,063 |
| TN-55(R) polypeptide | 1,000 | 9,049 cpm |
|  | 10,000 | 6,067 |
|  | 100,000 | 2,253 |
|  | 1,000,000 | 1,489 |
|  | 10,000,000 | 1,021 |
| Negative control |  | 1,249 cpm |

(2) Capacity of Promotion of Production of Prostaglandin $E_2$

The capacity of promotion of prostaglandin $E_2$ production was measured by the method described in Experiment 2. The results are shown in Table 9. As is clear from the results, the TN-55(F) polypeptide, TN-55(K) polypeptide and TN-55(R) polypeptide show almost no capacity of induction of production of prostaglandin $E_2$.

TABLE 9

| Polypeptide | Final dilution fold | Content of produced prostaglandin $E_2$ |
| --- | --- | --- |
| TN-55(F) polypeptide | 500 | 0.74 ng/ml |
|  | 5,000 | 0.57 |
|  | 50,000 | 0.47 |
|  | 500,000 | 0.61 |
|  | 5,000,000 | 1.12 |
| TN-55(K) polypeptide | 500 | 0.60 ng/ml |
|  | 5,000 | 0.42 |
|  | 50,000 | 0.81 |
|  | 500,000 | 0.59 |
|  | 5,000,000 | 0.56 |
| TN-55(R) polypeptide | 500 | 0.40 ng/ml |
|  | 5,000 | 0.68 |
|  | 50,000 | 0.40 |
|  | 500,000 | 0.54 |
|  | 5,000,000 | 0.56 |
| Negative control |  | 0.62 ng/ml |

As is clear from the above experimental results, the above polypeptides of this invention show almost no capacity of induction of production of prostaglandin $E_2$ even in an amount in which it exhibits potent activation of lymphocyte, and hence, these products are a polypeptide having very characteristic properties.

For simplification of the description, the following abbreviations are used in the present specification and claims.

| A: | adenine |
| --- | --- |
| C: | cytosine |
| G: | guanine |
| T: | thymine |
| DNA: | deoxyribonucleic acid |
| cDNA: | complementary DNA |
| RNA: | ribonucleic acid |
| mRNA: | messenger RNA |
| ATP: | adenosine triphosphate |
| dATP: | deoxyadenosine triphosphate |
| dCTP | deoxycytidine triphosphate |
| dGTP | deoxyguanosine triphosphate |
| dTTP | deoxythymidine triphosphate |
| bp: | base pairs |
| kbp: | kilobase pairs. |
| kD: | kilodaltons |
| SDS | sodium laurylsulfate |

This invention is illustrated by the following Examples and Reference Examples, but should not be construed to be limited thereto.

EXAMPLE 1

Production of TN-55 Polypeptide

TN-55 polypeptide having an amino acid sequence of the formula [IV] in Table 4 was produced by the following method.

(1) Construction of Expression Plasmid for Transformation

The recombinant plasmid pHIP312EC in Reference Example 2 was used as the starting material. The codon (GAC) encoding the 9th amino acid (Asp) at the C-terminus of human interleukin 1 polypeptide in said starting plasmid DNA was exchanged for the codon (TAC) corresponding to tyrosine by a site-specific mutation method similar to the method of Kunkel et al. (cf. Kunkel, T. A. et al., Methods in Enzymol., Vol. 154, 367, 1987), by which the expression plasmid for production of TN-55 polypeptide (pHTN55) was constructed.

The detail of the construction method is as follows.

The site-specific mutation was carried out by using MUTA-GENE In Vitro Mutagenesis Kit (manufactured by Bio-Rad Labs., USA). The plasmid pHIP312EC was digested with restriction enzymes PvuII and HindIII to isolate a DNA fragment containing a human interleukin 1 polypeptide-coding region and an *E. coli* tryptophane operon promoter region. This DNA fragment was inserted into M13mp19 vector between the restriction enzyme HindIII recognition site and the restriction enzyme HincII recognition site. *E. coli* JM105 strain was infected with this recombinant DNA and then cultivated, and the resulting phage was collected. *E. coli* JM105 strain was infected with this phage and cultivated in 2xTY medium [composition: 1.6% tryptone, 1% yeast extract, 0.5% sodium chloride] which contained uridine (1 µg/ml) and chloramphenicol (20 µg/ml) at 37° C. for 5 hours, and the phage DNA was isolated from the culture supernatant, and thereby there was obtained the phage DNA of about 2 µg per 10 ml of the culture supernatant.

Separately, an oligodeoxyribonucleotide having a nucleotide sequence of the following formula [B] was chemically synthetized by a conventional method.

5'-CTATCACTTACTTTCA-3'  [B]

This nucleotide sequence was identical with the sequence of 779th to 794th bases in the nucleotide sequence in Table 8 except the 787th base. This chemically synthesized DNA was designated as "mutated primer".

Phosphoric group was added to the mutated primer at 5'-terminus thereof, and the primer was incubated with the above-prepared phage DNA in an anneal buffer [composition: 20 mM Tris-HCl buffer (pH 7.4) containing 2 mM magnesium chloride and 50 mM sodium chloride] at 70° C. for 10 minutes, and the mixture was gradually cooled to 30° C. at a lowering rate of 1° C./minute, by which the primer was ligated with the phage DNA. The phage DNA was treated with T4 DNA polymerase and T4 DNA ligase in the presence of dGTP, dATP, dCTP, dTTP and ATP etc. whereby DNA complementary to the phase DNA was synthesized to form a circular double-stranded DNA. *E. coli* JM105 strain was infected with this cyclic double-stranded DNA, and each clone was cultivated and from the cultivated cells there was isolated a replicative mutated form of double-stranded DNA.

The nucleotide sequence of the DNA including the protein coding region was determined by using single-stranded DNA isolated from the culture supernatant by which it was confirmed that it had a nucleotide sequence encoding TN-55 polypeptide.

By digesting the replicative form of double-stranded DNA with restriction enzymes HpaI and XhoI, there was taken out a DNA fragment containing the protein coding region. This DNA fragment is designated as "TN-55 DNA fragment".

Separately, by digesting the recombinant plasmid pHIPH383a in Reference Example 1 with restriction enzymes HpaI and XhoI, there was taken out a large DNA fragment containing ampicillin resistance gene and replication origin. This DNA fragment was ligated by T4 DNA ligase with the above TN-55 DNA fragment to construct expression plasmid "pHTN55".

This expression plasmid pHTN55 was introduced into *E. coli* HB101 strain to prepare a transformant by the following method. That is, *E. coli* HB101 strain was inoculated to LB medium [composition: 1% tryptone, 0.5% yeast extract, 1% sodium chloride (pH 7.5)] and incubated at 30° C. overnight. The cell suspension (1 ml) was inoculated to LB medium (100 ml) and cultivated at 30° C. until the turbidity (absorbance at 600 nm) became about 0.6. The cultivated medium was allowed to stand in ice water for 30 minutes and centrifuted to separate cells. The cells were re-suspended in 50 mM calcium chloride solution (50 ml) and the mixture was allowed to stand in ice water for 60 minutes and centrifuged to separate cells. The cells were suspended in 50 mM calcium chloride solution containing 20% glycerin (10 ml). To the suspension was added the above expression plasmid pHTN55, and the mixture was incubated in ice water for 20 minutes and further at room temperature for 10 minutes, and thereto was added LB medium. The mixture was cultivated with shaking at 37° C. for 60 minutes. An aliquot of the resulting cell suspension was spread on LB agar plate (agar concentration 1.5%) containing ampicillin (25 µg/ml) and cultivated at 37° C. overnight to obtain ampicillin resistant clone. This ampicillin resistant clone, i.e. transformant, was designated as "HB101/pHTN55" and used for producing TN-55 polypeptide.

(2) Production of TN-55 Polypeptide

The HB101/pHTN55 for producing TN-55 polypeptide as obtained in the above (1) was cultivated in LB medium at 37° C. overnight. The resulting cell suspension was inoculated in about 100-fold volume of a nutrient medium [composition: 1.5% disodium phosphate.12 hydrate, 0.3% monopotassium phosphate, 0.1% ammonium chloride, 2 mg/l vitamin $B_1$, 0.5% casamic acid, 2 mM magnesium sulfate, 0.1 mM calcium chloride, 1% tryptone, 0.5% yeast extract, 1% sodium chloride, 0.4% glycerin] and thereto was added indol-3-acrylic acid at a final concentration of 20 µg/ml, and the mixture was cultivated for 28 hours. The cells were collected by centrifugation and suspended in 50 mM Tris-HCl buffer (pH 8.0) containing 0.1% lysozyme and 30 mM sodium chloride. The mixture was allowed to stand in ice water for 30 minutes and the cells were destroyed by repeating freezing in dry ice/ethanol bath and thawing at 37° C. To the mixture was added 1/50 volume of 10% polyethyleneimine, and the mixture was allowed to stand and centrifuged to remove cell debris etc. To the extract thus obtained was added ammonium sulfate until 70% saturation, and the mixture was allowed to stand and centrifuged to collect the precipitates. The precipitates were dissolved in distilled water, dialyzed against 5 mM phosphate buffered saline (pH 6.5) [hereinafter referred to "PBS"], and then subjected to gel filtration with Sephacryl S-200 column (manufactured by Pharmacia, Sweden). From a fraction corresponding to the molecular weight of about 15 to 20 kD, a solution containing TN-55 polypeptide was collected and charged to DEAE-Sepharose CL-6B column (Pharmacia) which was previously equilibrated with 5 mM phosphate buffer (pH 6.5) (hereinafter referred to as "PB"), and thereafter the column was washed with PB. The TN-55 polypeptide adsorbed to the column was eluted with PB having 0 to 0.5 M concentration gradient of sodium chloride. As a result, polypeptide having a molecular weight identical with the theoretical molecular weight of TN-55 polypeptide was eluted in two fractions. The fraction eluted with a lower concentration of sodium chloride was designated as "TN-55(a) polypeptide fraction", and the fraction eluted with a higher concentration of sodium chloride was designated as "TN-55(b) polypeptide fraction".

The TN-55(a) polypeptide fraction was dialyzed against 5 mM phosphate buffer (pH 5.7) (hereinafter referred to as "PB5"), charged to S-Sepharose First Flow column (Pharmacia) which was previously equilibrated with PB5, and then eluted with PB5 having 0 to 0.25 M concentration gradient of sodium chloride. The fraction of TN-55(a) polypeptide was collected and concentrated by ultrafiltration, and thereafter, purified by gel filtration with Toyopearl HW-55 column (manufactured by TOSOH, Japan) to obtain a highly purified product which had no impurity when analyzed with SDS-polyacrylamide gel electrophoresis.

The purified polypeptide obtained from TN-55(a) polypeptide fraction was subjected to the above-mentioned Experiments (1) and (2).

By the experiments, it was confirmed that the polypeptide was TN-55 polypeptide.

EXAMPLE 2

Production of Deamidated Product of TN-55 Polypeptide

By the following method there was isolated a modified polypeptide, i.e. TN-55 polypeptide in which 36th amino acid at the N-terminus was exchanged for Asp (hereinafter referred to as "TN-55Asp polypeptide").

From the TN-55(b) polypeptide fraction eluted with a higher concentration of sodium chloride by DEAE-Sepharose CL-6B column chromatography in Example 1-(2), there was isolated a polypeptide in the same manner as described in Example 1-(2). That is, a highly purified product was obtained by S-Sepharose First Flow column chromatography and gel filtration with Toyopearl HW-55 column.

As to the purified polypeptide from the TN-55(b) polypeptide fraction, the amino acid sequence was sequentially analyzed from the N-terminus by Edman degradation method. As a result, the polypeptide had the following amino acid sequence of from the N-terminus to the 40th amino acid.

| Ser | Ser | Pro | Phe | Ser | Phe | Leu | Ser | Asn | Val |
|---|---|---|---|---|---|---|---|---|---|
| Lys | Tyr | Asn | Phe | Met | Arg | Ile | Ile | Lys | Tyr |
| Glu | Phe | Ile | Leu | Asn | Asp | Ala | Leu | Asn | Gln |
| Ser | Ile | Ile | Arg | Ala | Asn | Asp | Gln | Tyr | Leu |

Thus, the 36th amino acid from the N-terminus was identified as Asp. Accordingly, it was concluded that the purified polypeptide was TN-55Asp polypeptide. This TN-55Asp polypeptide showed an isoelectric point of 5.4±0.2 when measured by an isolectric focusing.

EXAMPLE 3

Production of TN-55(141) Polypeptide

By the following method, there was isolated a polypeptide having an amino acid sequence of the formula [III] in Table 3 (wherein X is Asn and Y is Tyr), i.e. TN-55 polypeptide in which a peptide having fourteen amino acid residues at the N-terminus and a peptide having four amino acid residues at the C-terminus were deleted [hereinafter referred to as "TN-55(141) polypeptide"].

(1) Construction of Expression Plasmid

The recombinant plasmid pHL4 inserted with a cloned cDNA encoding human interleukin 1 precursor polypeptide as prepared by the method disclosed in European Patent Publication 0188920 was digested with a restiction enzyme PstI to cut out the cDNA region. The human interleukin 1 precursor polypeptide encoded by this cDNA has the amino acid sequence and nucleotide sequence as shown in Table 8. The cloned cDNA was digested with restriction enzymes EcoRI and Sau96I to isolate DNA fragment corresponding to the 398th to 769th bases in the nucleotide sequence shown in Table 8.

This DNA was ligated by T4 DNA ligase with two kinds of chemically synthesized oligonucleotide adaptors of the following Formulae [C] and [D].

The chemically synthesized oligonucleotide adaptors C] and [D] have the following nucleotide sequences:

```
5'-AAATTATGAGGATCATCAAATACG
   3'-TAATACTCCTAGTAGTTTATGCTTAA        [C]
``` and

```
5'-GGCCACCCTCTATCACTTACTTT-
   CAGATACTGTGATGACTCGA
   3'-GTGGGAGATAGTGAATGAAAGT-
   CTATGACACTACTGAGCTCTAG              [D]
```

The DNA fragment thus obtained was designated as "IL1(141) fragment".

Expression vector pEP302 was prepared by the method of Furutani et al. (cf. Furutani, Y. et al., Nucleic Acids Res., Vol. 13, 5869, 1985) and it was digested with restriction enzymes HpaI and BamHI to isolate a large DNA fragment containing E. coli tryptophane operon promoter region and ampicillin resistance gene. This fragment was ligated by T4 DNA ligase with a chemically synthesized oligonucleotide adaptor of the following Formula [E].

```
5'-AACTAGTACGCAAGTTCACGTAAAAG-
   GAGGTTT
   3'-TTGATCATGCGTTCAAGT-
   GCATTTTCCTCCAAATT                   [E]
```

The DNA fragment was further ligated by T4 DNA ligase with the above IL1(141) fragment, and thereby, there was constructed an expression plasmid for producing TN-55(141) polypeptide (cf. the accompanying FIG. 1). This expression plasmid was designated as "pHTN55(141)".

(2) Production of TN-55(141) Polypeptide

A transformant was prepared by using the expression plasmid pHTN55(141) prepared in the above (1) in the same manner as described in Example 1, and the transformant was cultivated likewise, and TN-55(141) polypeptide was isolated from the culture cells.

As to the purified TN-55(141) polypeptide, the amino acid sequence of the N-terminal region was analyzed by Edman degradation method. As a result, the polypeptide showed the following amino acid sequence of from the N-terminus to the 40th amino acid, which was well identical to the amino acid sequence of the formula [III] in Table 3 (X in Table 3 is Asn).

| Met | Arg | Ile | Ile | Lys | Tyr | Glu | Phe | Ile | Leu |
|---|---|---|---|---|---|---|---|---|---|
| Asn | Asp | Ala | Leu | Asn | Gln | Ser | Ile | Ile | Arg |
| Ala | Asn | Asp | Gln | Tyr | Leu | Thr | Ala | Ala | Ala |
| Leu | His | Asn | Leu | Asp | Glu | Ala | Val | Lys | Phe |

Besides, when it was digested with carboxypeptidase and the amino acid thereof was analyzed, there was detected leucine.

During the purification step of the TN-55(141) polypeptide, it was confirmed that a deamidated product having an acidic isoelectric point was present like in Example 2. When the amino acid sequence of the deamidated polypeptide was analyzed, it was confirmed that the 22nd amino acid at the N-terminus was exchanged for Asp.

The TN-55(141) polypeptide had an isoelectric point of 5.4±0.2, and the deamidated polypeptide had an isoelectric point of 5.2±0.2.

EXAMPLE 4

Production of other modified polypeptides of α-type human interleukin 1.

Other modified polypeptides of α-type human interleukin 1 in which 151st amino acid (Asp) at the C-terminus was exchanged for Phe, Lys or Arg were produced. The polypeptides exchanged the 151st Asp for Phe, Lys, and Arg are designated as "TN-55(F) polypeptide", "TN-55(K) polypeptide" and "TN-55(R) polypeptide", respectively, as mentioned hereinbefore. Expression plasmids for production of TN-55(F) polypeptide, TN-55(K) polypeptide and TN-55(R) polypeptide were constructed by exchanging the codon (GAC) encoding the 9th amino acid (Asp) at the C-terminus of α-type human interleukin 1 for the codon (TTC) corresponding to phenylalanine, the codon (AAA) corresponding to lysine or the codon (AGA) corresponding to arginine, respectively, according to a site-specific mutation method. The method for the construction of the expression plasmids was mentioned in Example 1, except for using the following chemically synthetized oligodeoxyribonucleotides as a mutated primer instead of using "mutated primer [B]". The mutated primers represented by 5'-TCTATCACTTTCTTTCAGATA-3', 5'-TCTATCACTAAATTTCAGATA-3' and 5'-TCTATCACTAGATTTCAGATA-3' were used for construction of the expression plasmids for production of TN-55(F) polypeptide, TN-55(K) polypeptide and TN-55(R) polypeptide, respectively.

Each expression plasmid was introduced into E. coli HB101 strain to prepare respective transformants by the calcium chloride method as mentioned in Example 1. The TN-55(F) polypeptide, TN-55(K) polypeptide and TN-55(R) polypeptide were produced by cultivating the obtained each transformant as mentioned in Example 1.

REFERENCE EXAMPLE 1

Construction of Expression Plasmid pHIPH383a

A recombinant plasmid pHL4 inserted with a cloned cDNA encoding human interleukin 1 precursor polypeptide (cf. Table 8) was digested with a restriction enzyme PstI to cut out the cDNA region. [Said recombinant plasmid pHL4 being described in European Patent Publication 0188920, Example 1-(6)] The cloned cDNA was digested with restriction enzymes EcoRI and BstNI to isolate a DNA fragment which corresponds to the 398th to 808th bases in the nucleotide sequence in Table 8.

This DNA fragment was ligated by T4 DNA ligase with two kinds of chemically synthesized oligonucleotide adaptors having the following formula [F] and [G]. The DNA fragment thus obtained was designated as "SD-IL1 fragment". The chemically synthesized oligonucleotide adaptor of the formula [F] was a DNA adaptor prepared by ligating five kinds of DNA fragments of the following formula [a] to [e] in order (hereinafter referred to as "chemically synthesized DNA [F]").

```
5'-AACTAGTACGCAAGTTCAC
3'-TTGATCATGCGTTCAAGTGCATT          [a]

5'-GTAAAAGGAGGTTTAAA
3'-TTCCTCCAAATTTAATAC              [b]

5'-TTATGTCATCACCTTTTAG
3'-AGTAGTGGAAAATCGAAGG             [c]

5'-CTTCCTGAGCAATGT-
    GAAATACAACTTTA
3'-ACTCGTTACACTTTATGTT-
    GAAATACTC                       [d]

5'-TGAGGATCATCAAATACG
3'-CTAGTAGTTTATGCTTAA               [e]
```

The chemically synthesized oligonucleotide adaptor of the formula [G] has the following nucleotide sequence.

```
5'-AGGCGTGATGACTCGA
3'-CCGCACTACTGAGCTCTAG             [G]
```

Figure 2:
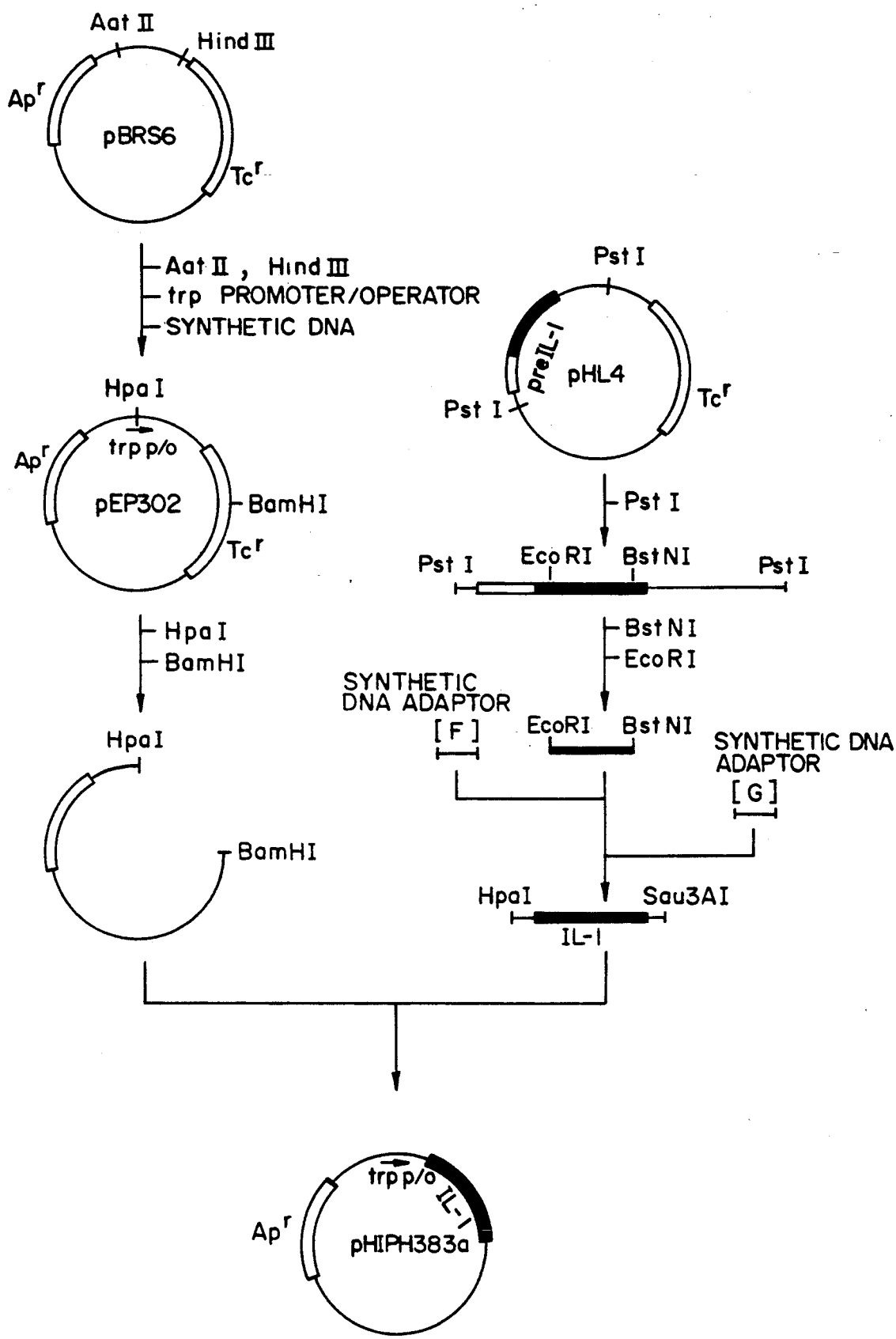
FIG. 2 shows steps of the construction of expression plasmid pHIPH383a of this invention, wherein the synthetic DNA adaptors [F] and [G] are the chemically synthesized oligonucleotide adaptors as described in Reference Example 1.

Separately, expression vector pEP302 (which was prepared by the method described in Nucleic Acids Res., Vol. 13, 5869, 1985) was digested with restriction enzymes HpaI and BamHI to isolate a large DNA fragment containing E. coli tryptophane operon promoter region and ampicillin resistance gene (hereinafter referred to as "vector fragment"). This vector fragment was ligated by T4 DNA ligase with the above SD-IL1 fragment, by which there was constructed an expression plasmid for producing human interleukin 1 polypeptide (cf. the accompanying FIG. 2).

This expression plasmid was designated as "pHIPH383a".

REFERENCE EXAMPLE 2

Construction of Expression Plasmid pHIP312EC

Plasmid pBR322 was digested with restriction enzymes AvaI and PvuII to isolate a large DNA fragment (about 3.7 kbp). Both ends of this DNA fragment were digested to blunt ends with DNA polymerase I (klenow fragment) and dGTP, dATP, dCTP, dTTP and then ligated by using T4 DNA ligase to prepare a plasmid vector in which a region for controllig the copy number at around replication origin of pBR322 was deleted (hereinafter referred to as "pBRS6")

The plasmid vector pBRS6 [which was prepared by the method described in European Patent Publication 0188920, Example 1-(5)] was digested with a restriction enzyme EcoRI to give straight chain DNA, and both ends thereof were digested to blunt ends by treating with DNA polymerase I (Klenow fragment) and dGTP, dATP, dCTP, dTTP. To both ends of this DNA fragment was ligated by T4 DNA ligase an oligonucleotide linker of the following formula [H].

The chemically synthesized linker had the following nucleotide sequence.

5'-CCTCGAGG-3'    [H]

Subsequently, the DNA fragment thus obtained was digested with restriction enzymes PstI and XhoI to isolate a large DNA fragment containing tetracycline resistance gene. This DNA fragment was designated as "pBRS6-fragment".

Figure 3:
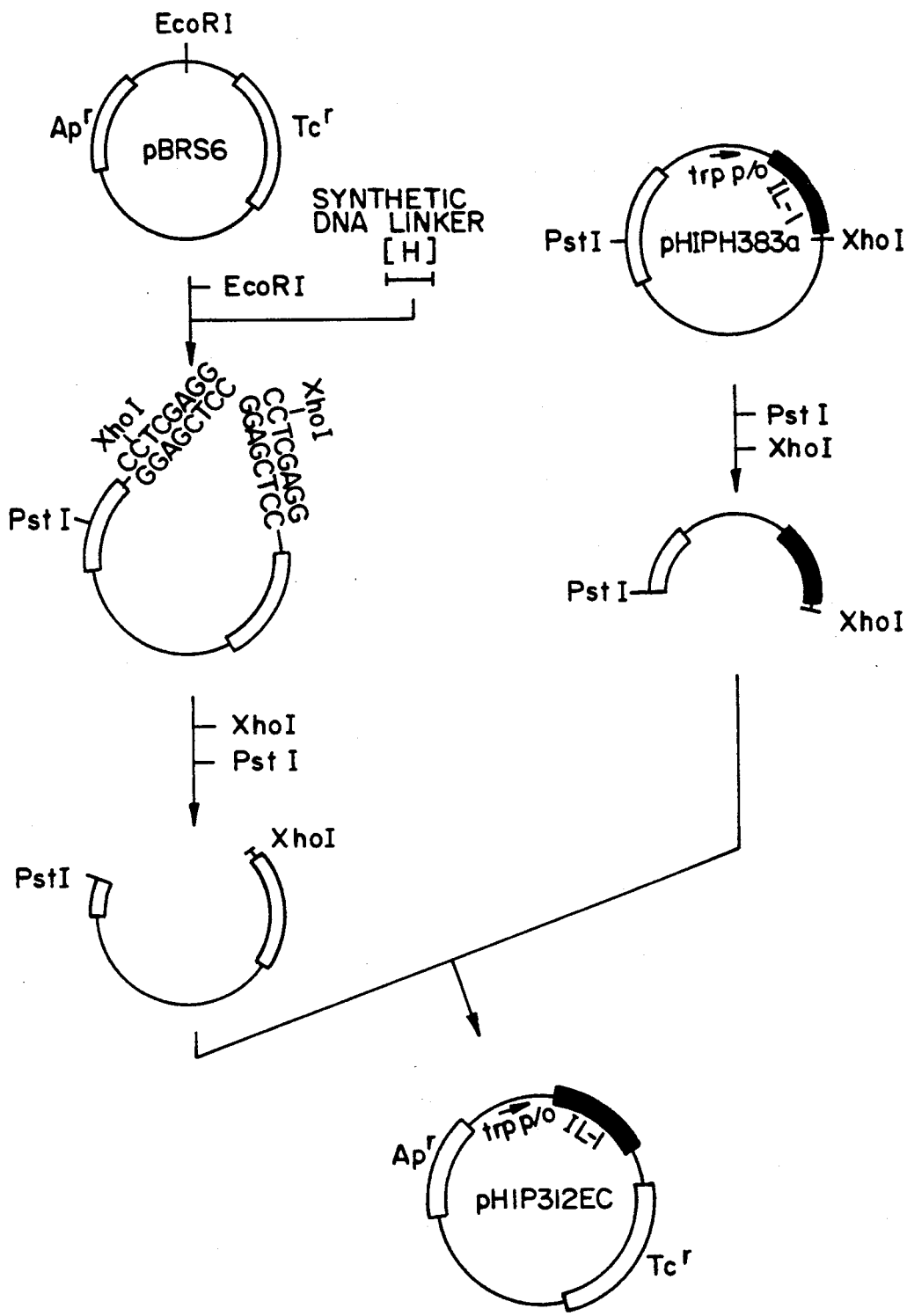
FIG. 3 shows steps of the construction of expression plasmid pHIP312EC of this invention, wherein the synthetic DNA linker [H] is the chemically synthesized oligonucleotide linker as described in Reference Example 2.

Separately, the recombinant plasmid pHIPH383a disclosed in Reference Example 1 was digested with restriction enzymes PstI and XhoI to isolate a DNA fragment containing a region encoding human interleukin 1 polypeptide. This DNA fragment was ligated with the above pBRS6-fragment, by which there was constructed an expression plasmid for producing human interleukin 1 polypeptide which contained tetracycline resistance gene (cf. the accompanying FIG. 3).

This expression plasmid was designated a "pHIP31-2EC".

TABLE 8

Nucleotide sequence and amino acid sequence of cDNA encoding human interleukin 1 (α-type) precursor polypeptide:

| 1 | | | | | | | | | 10 | |
|---|---|---|---|---|---|---|---|---|---|---|
| Met | Ala | Lys | Val | Pro | Asp | Met | Phe | Glu | Asp | |
| ATG | GCC | AAA | GTT | CCA | GAC | ATG | TTT | GAA | GAC | (30) |
| Leu | Lys | Asn | Cys | Tyr | Ser | Glu | Asn | Glu | 20 Glu | |
| CTG | AAG | AAC | TGT | TAC | AGT | GAA | AAT | GAA | GAA | (60) |
| Asp | Ser | Ser | Ser | Ile | Asp | His | Leu | Ser | 30 Leu | |
| GAC | AGT | TCC | TCC | ATT | GAT | CAT | CTG | TCT | CTG | (90) |
| Asn | Gln | Lys | Ser | Phe | Tyr | His | Val | Ser | 40 Tyr | |
| AAT | CAG | AAA | TCC | TTC | TAT | CAT | GTA | AGC | TAT | (120) |
| Gly | Pro | Leu | His | Glu | Gly | Cys | Met | Asp | 50 Gln | |
| GGC | CCA | CTC | CAT | GAA | GGC | TGC | ATG | GAT | CAA | (150) |
| Ser | Val | Ser | Leu | Ser | Ile | Ser | Glu | Thr | 60 Ser | |
| TCT | GTG | TCT | CTG | AGT | ATC | TCT | GAA | ACC | TCT | (180) |
| Lys | Thr | Ser | Lys | Leu | Thr | Phe | Lys | Glu | 70 Ser | |
| AAA | ACA | TCC | AAG | CTT | ACC | TTC | AAG | GAG | AGC | (210) |
| Met | Val | Val | Val | Ala | Thr | Asn | Gly | Lys | 80 Val | |
| ATG | GTG | GTA | GTA | GCA | ACC | AAC | GGG | AAG | GTT | (240) |
| Leu | Lys | Lys | Arg | Arg | Leu | Ser | Leu | Ser | 90 Gln | |
| CTG | AAG | AAG | AGA | CGG | TTG | AGT | TTA | AGC | CAA | (270) |
| Ser | Ile | Thr | Asp | Asp | Asp | Leu | Glu | Ala | 100 Ile | |
| TCC | ATC | ACT | GAT | GAT | GAC | CTG | GAG | GCC | ATC | (300) |
| Ala | Asn | Asp | Ser | Glu | Glu | Glu | Ile | Ile | 110 Lys | |
| GCC | AAT | GAC | TCA | GAG | GAA | GAA | ATC | ATC | AAG | (330) |
| Pro | Arg | Ser | Ser | Pro | Phe | Ser | Phe | Leu | 120 Ser | |
| CCT | AGG | TCA | TCA | CCT | TTT | AGC | TTC | CTG | AGC | (360) |
| Asn | Val | Lys | Tyr | Asn | Phe | Met | Arg | Ile | 130 Ile | |
| AAT | GTG | AAA | TAC | AAC | TTT | ATG | AGG | ATC | ATC | (390) |
| Lys | Tyr | Glu | Phe | Ile | Leu | Asn | Asp | Ala | 140 Leu | |
| AAA | TAC | GAA | TTC | ATC | CTG | AAT | GAC | GCC | CTC | (420) |
| Asn | Gln | Ser | Ile | Ile | Arg | Ala | Asn | Asp | 150 Gln | |

TABLE 8-continued

|     |     |     |     |     |     |     |     |     | 160 |       |
|-----|-----|-----|-----|-----|-----|-----|-----|-----|-----|-------|
|     | AAT | CAA | AGT | ATA | ATT | CGA | GCC | AAT | GAT | CAG (450) |
| Tyr | Leu | Thr | Ala | Ala | Ala | Leu | His | Asn | Leu |       |
| TAC | CTC | ACG | GCT | GCT | GCA | TTA | CAT | AAT | CTG | (480) |
|     |     |     |     |     |     |     |     |     | 170 |       |
| Asp | Glu | Ala | Val | Lys | Phe | Asp | Met | Gly | Ala |       |
| GAT | GAA | GCA | GTG | AAA | TTT | GAC | ATG | GGT | GCT | (510) |
|     |     |     |     |     |     |     |     |     | 180 |       |
| Tyr | Lys | Ser | Ser | Lys | Asp | Asp | Ala | Lys | Ile |       |
| TAT | AAG | TCA | TCA | AAG | GAT | GAT | GCT | AAA | ATT | (540) |
| Thr | Val | Ile | Leu | Arg | Ile | Ser | Lys | Thr | Gln |       |
| ACC | GTG | ATT | CTA | AGA | ATC | TCA | AAA | ACT | CAA | (570) |
|     |     |     |     |     |     |     |     |     | 200 |       |
| Leu | Tyr | Val | Thr | Ala | Gln | Asp | Glu | Asp | Gln |       |
| TTG | TAT | GTG | ACT | GCC | CAA | GAT | GAA | GAC | CAA | (600) |
|     |     |     |     |     |     |     |     |     | 210 |       |
| Pro | Val | Leu | Leu | Lys | Glu | Met | Pro | Glu | Ile |       |
| CCA | GTG | CTG | CTG | AAG | GAG | ATG | CCT | GAG | ATA | (630) |
|     |     |     |     |     |     |     |     |     | 220 |       |
| Pro | Lys | Thr | Ile | Thr | Gly | Ser | Glu | Thr | Asn |       |
| CCC | AAA | ACC | ATC | ACA | GGT | AGT | GAG | ACC | AAC | (660) |
|     |     |     |     |     |     |     |     |     | 230 |       |
| Leu | Leu | Phe | Phe | Trp | Glu | Thr | His | Gly | Thr |       |
| CTC | CTC | TTC | TTC | TGG | GAA | ACT | CAC | GGC | ACT | (690) |
|     |     |     |     |     |     |     |     |     | 240 |       |
| Lys | Asn | Tyr | Phe | Thr | Ser | Val | Ala | His | Pro |       |
| AAG | AAC | TAT | TTC | ACA | TCA | GTT | GCC | CAT | CCA | (720) |
|     |     |     |     |     |     |     |     |     | 250 |       |
| Asn | Leu | Phe | Ile | Ala | Thr | Lys | Gln | Asp | Tyr |       |
| AAC | TTG | TTT | ATT | GCC | ACA | AAG | CAA | GAC | TAC | (750) |
|     |     |     |     |     |     |     |     |     | 260 |       |
| Trp | Val | Cys | Leu | Ala | Gly | Gly | Pro | Pro | Ser |       |
| TGG | GTG | TGC | TTG | GCA | GGG | GGG | CCA | CCC | TCT | (780) |
|     |     |     |     |     |     |     |     |     | 270 |       |
| Ile | Thr | Asp | Phe | Gln | Ile | Leu | Glu | Asn | Gln |       |
| ATC | ACT | GAC | TTT | CAG | ATA | CTG | GAA | AAC | CAG | (810) |

271
Ala***
GCGTAG

In the above table, the number means amino acid number, the parenthesized number means the nucleotide number, and *** means translation stop codon.

What is claimed is:

1. A modified human interleukin 1α polypeptide having an amino acid sequence of the following formula [I]:

Formula [I]

Ser W Pro Phe Ser Phe Leu Ser Asn Val
Lys Tyr Asn Phe Met Arg Ile Ile Lys Tyr
Glu Phe Ile Leu Asn Asp Ala Leu Asn Gln
Ser Ile Ile Arg Ala X Asp Gln Tyr Leu
Thr Ala Ala Ala Leu His Asn Leu Asp Glu
Ala Val Lys Phe Asp Met Gly Ala Tyr Lys
Ser Ser Lys Asp Asp Ala Lys Ile Thr Val
Ile Leu Arg Ile Ser Lys Thr Gln Leu Tyr
Val Thr Ala Gln Asp Glu Asp Gln Pro Val
Leu Leu Lys Glu Met Pro Glu Ile Pro Lys
Thr Ile Thr Gly Ser Glu Thr Asn Leu Leu
Phe Phe Trp Glu Thr His Gly Thr Lys Asn
Tyr Phe Thr Ser Val Ala His Pro Asn Leu
Phe Ile Ala Thr Lys Gln Asp Tyr Trp Val
Cys Leu Ala Gly Gly Pro Pro Ser Ile Thr
Y Phe Gln Ile Leu Glu Asn Gln Ala in which W means Ser, X means Asn, and Y means Tyr, Phe, Lys, or Arg.

2. The polypeptide according to claim 1, which has an amino acid sequence of the formula [I] wherein Y is Tyr.

3. A modified human interleukin 1α polypeptide having the sequence

Formula III

Met Arg Ile Ile Lys Tyr Glu Phe Ile Leu
Asn Asp Ala Leu Asn Gln Ser Ile Ile Arg
Ala X Asp Gln Tyr Leu Thr Ala Ala Ala
Leu His Asn Leu Asp Glu Ala Val Lys Phe
Asp Met Gly Ala Tyr Lys Ser Ser Lys Asp
Asp Ala Lys Ile Thr Val Ile Leu Arg Ile
Ser Lys Thr Gln Leu Tyr Val Thr Ala Gln
Asp Glu Asp Gln Pro Val Leu Leu Lys Glu
Met Pro Glu Ile Pro Lys Thr Ile Thr Gly
Ser Glu Thr Asn Leu Leu Phe Phe Trp Glu
Thr His Gly Thr Lys Asn Tyr Phe Thr Ser
Val Ala His Pro Asn Leu Phe Ile Ala Thr
Lys Gln Asp Tyr Trp Val Cys Leu Ala Gly
Gly Pro Pro Ser Ile Thr Y Phe Gln Ile
Leu in which X is Asn or Asp and Y is Tyr.

* * * * *

UNITED STATES PATENT AND TRADEMARK OFFICE
CERTIFICATE OF CORRECTION

PATENT NO. : 5,290,917
DATED : March 1, 1994
INVENTOR(S) : Michiko Yamayoshi, et al.

It is certified that error appears in the above-indentified patent and that said Letters Patent is hereby corrected as shown below:

On the Title Page, after Section [22], insert the following: --[30]  Foreign Application Priority Date
Feb. 3, 1988 [JP]   Japan.......024613/1988--

Column 3, line 17: "th" should read --the--

Column 4, line 47: delete "("

Column 5, line 2: " ; " should read --$\lambda$--

Column 8, line 55: after "pairs" delete --.--

Column 9, line 15: "In Vitro" should read --In Vitro--

Column 9, line 17: "Pvu" should read --Pvu--

Column 9, line 68: "Hpa" and "Xho" should read --Hpa-- and --Xho--

Column 10, line 6: "Hpa" and "Xho" should read --Hpa-- and --Xho--

Column 10, line 45: ".12" should read --·12--

UNITED STATES PATENT AND TRADEMARK OFFICE
CERTIFICATE OF CORRECTION

PATENT NO. : 5,290,917
DATED : March 1, 1994
INVENTOR(S) : Michiko Yamayoshi, et al.

It is certified that error appears in the above-indentified patent and that said Letters Patent is hereby corrected as shown below:

```
Column 12, line 35:   before "C" insert --[--
Column 13, line 39:   "C-"  should read --N- --
Column 14, line 23:   "[e]in"  should read
--[e] in--
Column 16, line 16:   "a"  should read --as--
```

Signed and Sealed this

Fourth Day of October, 1994

Attest:

BRUCE LEHMAN

*Attesting Officer*   *Commissioner of Patents and Trademarks*